United States Patent [19]

Bundy

[11] 4,191,707
[45] Mar. 4, 1980

[54] 2-DECARBOXY-2-AMINOMETHYL-9-DEOXY-9-METHYLENE-16-PHENYL-PGF COMPOUNDS

[75] Inventor: Gordon L. Bundy, Portage, Mich.

[73] Assignee: The Upjohn Company, Kalamazoo, Mich.

[21] Appl. No.: 923,831

[22] Filed: Jul. 12, 1978

Related U.S. Application Data

[63] Continuation-in-part of Ser. No. 786,249, Apr. 11, 1977, Pat. No. 4,118,584.

[51] Int. Cl.$^2$ ............................................. C07C 87/45
[52] U.S. Cl. ........................................... 260/570.5 CA
[58] Field of Search ............................... 260/570.5 CA

[56] References Cited

U.S. PATENT DOCUMENTS 4,119,666  10/1978  Bundy ..................... 280/570.5 X Primary Examiner—Robert V. Hines
Attorney, Agent, or Firm—Robert A. Armitage

[57] ABSTRACT

The present invention relates to novel 2-decarboxy-2-aminomethyl-9-deoxy-9-methylene-16-phenyl-PGF compounds. These compounds are useful pharmacological agents, and are useful for the same purposes as the corresponding PGE-type compounds.

210 Claims, No Drawings

2-DECARBOXY-2-AMINOMETHYL-9-DEOXY-9-METHYLENE-16-PHENYL-PGF COMPOUNDS

CROSS REFERENCE TO RELATED APPLICATIONS

This application is a continuation-in-part of Ser. No. 786,249, filed Apr. 11, 1977, issued as U.S. Pat. No. 4,118,584 on Oct. 3, 1978.

The present invention relates to novel 2-decarboxy-2-aminomethyl-9-deoxy-9-methylene-16-phenyl-PGF compounds, the essential material constituting a disclosure of which is incorporated here by reference from U.S. Pat. No. 4,118,584.

I claim:

1. A prostaglandin analog of the formula

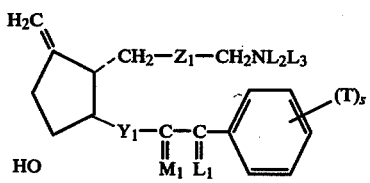

wherein $Y_1$ is trans-CH=CH—, —C≡C—, or —CH$_2$CH$_2$—;
wherein $M_1$ is

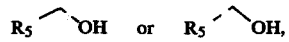

wherein $R_5$ is hydrogen or methyl;
wherein $L_1$ is

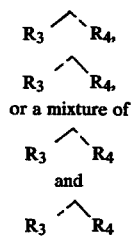

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —C≡C—CH$_2$—(CH$_2$)$_g$—CH$_2$—,
(8) —CH$_2$—C≡C—(CH$_2$)$_g$—CH$_2$—,

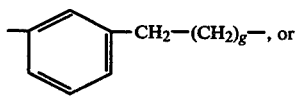 (9)

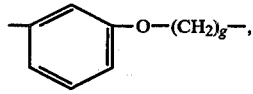 (10)

wherein g is one, 2, or 3;
wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;
wherein $L_2$ and $L_3$ are hydrogen, or alkyl of one to 4 carbon atoms, inclusive.

2. A prostaglandin analog according to claim 1, wherein $Y_1$ is —CH$_2$CH$_2$—.

3. A prostaglandin analog according to claim 2, wherein

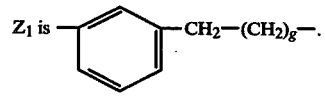

4. A prostaglandin analog according to claim 2, wherein

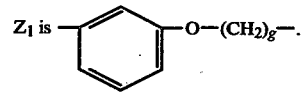

5. 2-Decarboxy-2-aminomethyl-9-deoxy-9-methylene-3,7-inter-m-phenylene-3-oxa-16-phenyl-4,5,6,17,18,19,20-heptanor-13,14-dihydro-PGF$_1$, a prostaglandin analog according to claim 4.

6. A prostaglandin analog according to claim 2, wherein $Z_1$ is cis—CH$_2$—CH=CH—(CH$_2$)$_g$—CH$_2$—.

7. 2-Decarboxy-2-aminomethyl-9-deoxy-9-methylene-cis-3,4-didehydro-16-phenyl-17,18,19,20-tetranor-13,14-dihydro-PGF$_1$, a prostaglandin analog according to claim 6.

8. A prostaglandin analog according to claim 2, wherein $Z_1$ is —CH$_2$—O—CH$_2$—(CH$_2$)$_g$—CH$_2$—.

9. 2-Decarboxy-2-aminomethyl-9-deoxy-9-methylene-5-oxa-16-phenyl-17,18,19,20-tetranor-13,14-dihydro-PGF$_1$, a prostaglandin analog according to claim 8.

10. A prostaglandin analog according to claim 2, wherein $Z_1$ is —C≡C—CH$_2$—(CH$_2$)$_g$—CH$_2$—.

11. 2-Decarboxy-2-aminomethyl-9-deoxy-9-methylene-5,6-didehydro-16-phenyl-17,18,19,20-tetranor-13,14-dihydro-PGF$_2$, a prostaglandin analog according to claim 10.

12. A prostaglandin analog according to claim 2, wherein $Z_1$ is —CH$_2$—C≡C—(CH$_2$)$_g$—CH$_2$—.

13. 2-Decarboxy-2-aminomethyl-9-deoxy-9-methylene-4,4,5,5-tetradehydro-16-phenyl-17,18,19,20-tetranor-13,14-dihydro-PGF$_1$, a prostaglandin analog according to claim 12.

14. A prostaglandin analog according to claim 2, wherein $Z_1$ is —(CH$_2$)$_3$—(CH$_2$)$_g$—CH$_2$—.

15. A prostaglandin analog according to claim 14, wherein $M_1$ is

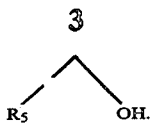

16. 2-Decarboxy-2-aminomethyl-9-deoxy-9-methylene-15-epi-16-phenyl-17,18,19,20-tetranor-13,14-dihydro-PGF$_1$, a prostaglandin analog according to claim 15.

17. A prostaglandin analog according to claim 14, wherein M$_1$ is

18. A prostaglandin analog according to claim 17, wherein s is zero or one and T is chloro, fluoro, or trifluoromethyl.

19. A prostaglandin analog according to claim 18, wherein g is 3.

20. 2-Decarboxy-2-aminomethyl-9-deoxy-9-methylene-2a,2b-dihomo-15-methyl-16-phenyl-17,18,19,20-tetranor-13,14-dihydro-PGF$_1$, a prostaglandin analog according to claim 19.

21. 2-Decarboxy-2-aminomethyl-9-deoxy-9-methylene-2a,2b-dihomo-16-phenyl-17,18,19,20-tetranor-13,14-dihydro-PGF$_1$, a prostaglandin analog according to claim 19.

22. A prostaglandin analog according to claim 18, wherein g is one.

23. A prostaglandin analog according to claim 22, wherein at least one of R$_3$ and R$_4$ is methyl.

24. A prostaglandin analog according to claim 23, wherein R$_3$ and R$_4$ are both methyl.

25. 2-Decarboxy-2-aminomethyl-9-deoxy-9-methylene-16-methyl-16-phenyl-18,19,20-trinor-13,14-dihydro-PGF$_1$, a prostaglandin analog according to claim 24.

26. A prostaglandin analog according to claim 22, wherein at least one of R$_3$ and R$_4$ is fluoro.

27. A prostaglandin analog according to claim 26, wherein R$_3$ and R$_4$ are both fluoro.

28. 2-Decarboxy-2-aminomethyl-9-deoxy-9-methylene-16,16-difluoro-16-phenyl-17,18,19,20-tetranor-13,14-dihydro-PGF$_1$, a prostaglandin analog according to claim 27.

29. A prostaglandin analog according to claim 22, wherein R$_3$ and R$_4$ are both hydrogen.

30. A prostaglandin analog according to claim 29, wherein R$_5$ is methyl.

31. 2-Decarboxy-2-aminomethyl-9-deoxy-9-methylene-15-methyl-16-phenyl-17,18,19,20-tetranor-13,14-dihydro-PGF$_1$, a prostaglandin analog according to claim 30.

32. A prostaglandin analog according to claim 29, wherein R$_5$ is hydrogen.

33. 2-Decarboxy-2-aminomethyl-9-deoxy-9-methylene-16-phenyl-17,18,19,20-tetranor-13,14-dihydro-PGF$_1$, a prostaglandin analog according to claim 32.

34. A prostaglandin analog according to claim 2, wherein Z$_1$ is cis—CH=CH—CH$_2$—(CH$_2$)$_g$—CH$_2$—.

35. A prostaglandin analog according to claim 34, wherein M$_1$ is

36. A prostaglandin analog according to claim 35, wherein s is zero or one and T is chloro, fluoro, or trifluoromethyl.

37. A prostaglandin analog according to claim 36, wherein g is 3.

38. 2-Decarboxy-2-aminomethyl-9-deoxy-9-methylene-2a,2b-dihomo-15-epi-15-methyl-16-phenyl-17,18,19,20-tetranor-13,14-dihydro-PGF$_2$, a prostaglandin analog according to claim 37.

39. 2-Decarboxy-2-aminomethyl-9-deoxy-9-methylene-2a,2b-dihomo-15-epi-16-phenyl-17,18,19,20-tetranor-13,14-dihydro-PGF$_2$, a prostaglandin analog according to claim 37.

40. A prostaglandin analog according to claim 36, wherein g is one.

41. A prostaglandin analog according to claim 40, wherein at least one of R$_3$ and R$_4$ is methyl.

42. 2-Decarboxy-2-aminomethyl-9-deoxy-9-methylene-15-epi-16-methyl-16-phenyl-18,19,20-trinor-13,14-dihydro-PGF$_2$, a prostaglandin analog according to claim 41.

43. A prostaglandin analog according to claim 40, wherein at least one of R$_3$ and R$_4$ is fluoro.

44. 2-Decarboxy-2-aminomethyl-9-deoxy-9-methylene-15-epi-16,16-difluoro-16-phenyl-17,18,19,20-tetranor-13,14-dihydro-PGF$_2$, a prostaglandin analog according to claim 43.

45. A prostaglandin analog according to claim 40, wherein R$_3$ and R$_4$ are both hydrogen.

46. 2-Decarboxy-2-aminomethyl-9-deoxy-9-methylene-15-epi-16-methyl-16-phenyl-17,18,19,20-tetranor-13,14-dihydro-PGF$_2$, a prostaglandin analog according to claim 45.

47. A prostaglandin analog according to claim 34, wherein M$_1$ is

48. A prostaglandin analog according to claim 47, wherein s is zero and T is chloro, fluoro, trifluoromethyl.

49. A prostaglandin analog according to claim 48, wherein g is 3.

50. A prostaglandin analog according to claim 49, wherein at least one of R$_3$ and R$_4$ is methyl.

51. 2-Decarboxy-2-aminomethyl-9-deoxy-9-methylene-2a,2b-dihomo-16-methyl-16-phenyl-18,19,20-trinor-13,14-dihydro-PGF$_2$, a prostaglandin analog according to claim 50.

52. A prostaglandin analog according to claim 49, wherein at least one of R$_3$ and R$_4$ is fluoro.

53. 2-Decarboxy-2-aminomethyl-9-deoxy-9-methylene-2a,2b-dihomo-16,16-difluoro-16-phenyl-17,18,19,20-tetranor-13,14-dihydro-PGF$_2$, a prostaglandin analog according to claim 52.

54. A prostaglandin analog according to claim 49, wherein R$_3$ and R$_4$ are both hydrogen.

55. 2-Decarboxy-2-aminomethyl-9-deoxy-9-methylene-2a,2b-dihomo-16-phenyl-17,18,19,20-tetranor-13,14-dihydro-PGF$_2$, a prostaglandin analog according to claim 54.

56. A prostaglandin analog according to claim 38, wherein g is one.

57. A prostaglandin analog according to claim 56, wherein at least one of R$_3$ and R$_4$ is methyl.

58. A prostaglandin analog according to claim 57, wherein $R_3$ and $R_4$ are both methyl.

59. 2-Decarboxy-2-aminomethyl-9-deoxy-9-methylene-16-methyl-16-phenyl-18,19,20-trinor-13,14-dihydro-$PGF_2$, a prostaglandin analog analog according to claim 58.

60. A prostaglandin analog according to claim according to claim 56, wherein at least one of $R_3$ and $R_4$ is fluoro.

61. A prostaglandin analog according to claim 60, wherein $R_3$ and $R_4$ are both fluoro.

62. A prostaglandin analog according to claim 61, wherein $R_5$ is methyl.

63. 2-Decarboxy-2-aminomethyl-9-deoxy-9-methylene-15-methyl-16,16-difluoro-16-phenyl-17,18,19,20-tetranor-13,14-dihydro-$PGF_2$, a prostaglandin analog according to claim 62.

64. A prostaglandin analog according to claim 61, wherein $R_5$ is hydrogen.

65. 2-Decarboxy-2-aminomethyl-9-deoxy-9-methylene-16,16-difluoro-16-phenyl-17,18,19,20-tetranor-13,14-dihydro-$PGF_2$, a prostaglandin analog according to claim 64.

66. A prostaglandin analog according to claim 56, wherein $R_3$ and $R_4$ are both hydrogen.

67. A prostaglandin analog according to claim 66, wherein $R_5$ is methyl.

68. 2-Decarboxy-2-aminomethyl-9-deoxy-9-methylene-15-methyl-16-phenyl-17,18,19,20-tetranor-13,14-dihydro-$PGF_2$, a prostaglandin analog according to claim 67.

69. A prostaglandin analog according to claim 66, wherein $R_5$ is hydrogen.

70. 2-Decarboxy-2-aminomethyl-9-deoxy-9-methylene-16-phenyl-17,18,19,20-tetranor-13,14-dihydro-$PGF_2$, a prostaglandin analog according to claim 69.

71. A prostaglandin analog according to claim 1, wherein $Y_1$ is —C≡C—.

72. A prostaglandin analog according to claim 71, wherein $Z_1$ is cis—CH=CH—$CH_2$—$(CH_2)_g$—$CF_2$—.

73. 2-Decarboxy-2-aminomethyl-9-deoxy-9-methylene-2,2-difluoro-16-phenyl-17,18,19,20-tetranor-13,14-didehydro-$PGF_2$, a prostaglandin analog according to claim 72.

74. A prostaglandin analog according to claim 71, wherein $Z_1$ is —$(CH_2)_3$—$(CH_2)_g$—$CF_2$—.

75. 2-Decarboxy-2-aminomethyl-9-deoxy-9-methylene-2,2-difluoro-16-phenyl-17,18,19,20-tetranor-13,14-didehydro-$PGF_1$, a prostaglandin analog according to claim 74.

76. A prostaglandin analog according to claim 71, wherein $Z_1$ is cis—$CH_2$—CH=CH—$(CH_2)_g$—$CH_2$—.

77. 2-Decarboxy-2-aminomethyl-9-deoxy-9-methylene-cis-4,5-didehydro-16-phenyl-17,18,19,20-tetranor-13,14-didehydro-$PGF_1$, a prostaglandin analog according to claim 76.

78. A prostaglandin analog according to claim 71, wherein $Z_1$ is —$CH_2$—O—$CH_2$—$(CH_2)_g$—$CH_2$—.

79. 2-Decarboxy-2-aminomethyl-9-deoxy-9-methylene-5-oxa-16-phenyl-17,18,19,20-tetranor-13,14-didehydro-$PGF_1$, a prostaglandin analog according to claim 78.

80. A prostaglandin analog according to claim 71, wherein $Z_1$ is —C≡C—$CH_2$—$(CH_2)_g$—$CH_2$—.

81. 2-Decarboxy-2-aminomethyl-9-deoxy-9-methylene-16-phenyl-17,18,19,20-tetranor-5,6,13,14-tetradehydro-$PGF_2$, a prostaglandin analog according to claim 80.

82. A prostaglandin analog according to claim 71, wherein $Z_1$ is —$CH_2$—C≡C—$(CH_2)_g$—$CH_2$—.

83. 2-Decarboxy-2-aminomethyl-9-deoxy-9-methylene-16-phenyl-17,18,19,20-tetranor-4,4,5,5,13,14-hexadehydro-$PGF_1$, a prostaglandin analog according to claim 82.

84. A prostaglandin analog according to claim 71, wherein $Z_1$ is —$(CH_2)_3$—$(CH_2)_g$—$CH_2$—.

85. A prostaglandin analog according to claim 84, wherein $M_1$ is

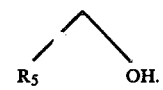

86. 2-Decarboxy-2-aminomethyl-9-deoxy-9-methylene-15-epi-16-phenyl-17,18,19,20-tetranor-13,14-didehydro-$PGF_1$, a prostaglandin analog according to claim 85.

87. A prostaglandin analog according to claim 84, wherein $M_1$ is

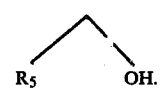

88. A prostaglandin analog according to claim 87, wherein s is zero or one and T is chloro, fluoro, or trifluoromethyl.

89. A prostaglandin analog according to claim 88, wherein g is 3.

90. 2-Decarboxy-2-aminomethyl-9-deoxy-9-methylene-2a,2b-dihomo-15-methyl-16-phenyl-17,18,19,20-tetranor-13,14-didehydro-$PGF_1$, a prostaglandin analog according to claim 89.

91. 2-Decarboxy-2-aminomethyl-9-deoxy-9-methylene-2a,2b-dihomo-15-methyl-16-phenyl-17,18,19,20-tetranor-13,14-didehydro-$PGF_1$, a prostaglandin analog according to claim 89.

92. A prostaglandin analog according to claim 88, wherein g is one.

93. A prostaglandin analog according to claim 92, wherein at least one of $R_3$ and $R_4$ is methyl.

94. A prostaglandin analog according to claim 93, wherein $R_3$ and $R_4$ are both methyl.

95. 2-Decarboxy-2-aminomethyl-9-deoxy-9-methylene-16-methyl-16-phenyl-18,19,20-trinor-13,14-didehydro-$PGF_1$, a prostaglandin analog according to claim 94.

96. A prostaglandin analog according to claim 92, wherein at least one of $R_3$ and $R_4$ is fluoro.

97. A prostaglandin analog according to claim 96, wherein $R_3$ and $R_4$ are both fluoro.

98. 2-Decarboxy-2-aminomethyl-9-deoxy-9-methylene-16,16-difluoro-16-phenyl-17,18,19,20-tetranor-13,14-didehydro-$PGF_1$, a prostaglandin analog according to claim 97.

99. A prostaglandin analog according to claim 92, wherein $R_3$ and $R_4$ are both hydrogen.

100. A prostaglandin analog according to claim 99, wherein $R_5$ is methyl.

101. 2-Decarboxy-2-aminomethyl-9-deoxy-9-methylene-15-methyl-16-phenyl-17,18,19,20-tetranor-13,14-didehydro-$PGF_1$, a prostaglandin analog according to claim 100.

102. A prostaglandin analog according to claim 99, wherein $R_5$ is hydrogen.

103. 2-Decarboxy-2-aminomethyl-9-deoxy-9-methylene-16-phenyl-17,18,19,20-tetranor-13,14-didehydro-PGF$_1$, a prostaglandin analog according to claim 102.

104. A prostaglandin analog according to claim 71, wherein Z$_1$ is cis—CH=CH—CH$_2$—(CH$_2$)$_g$—CH$_2$—.

105. A prostaglandin analog according to claim 104, wherein M$_1$ is

106. A prostaglandin analog according to claim 105, wherein s is zero or one and T is chloro, fluoro, trifluoromethyl.

107. A prostaglandin analog according to claim 106, wherein g is 3.

108. 2-Decarboxy-2-aminomethyl-9-deoxy-9-methylene-2a,2b-dihomo-15-epi-15-methyl-16-phenyl-17,18,19,20-tetranor-13,14-didehydro-PGF$_2$, a prostaglandin analog according to claim 107.

109. 2-Decarboxy-2-aminomethyl-9-deoxy-9-methylene-2a,2b-dihomo-15-epi-16-phenyl-17,18,19,20-tetranor-13,14-didehydro-PGF$_2$, a prostaglandin analog according to claim 107.

110. A prostaglandin analog according to claim 106, wherein g is one.

111. A prostaglandin analog according to claim 110, wherein at least one of R$_3$ and R$_4$ is methyl.

112. 2-Decarboxy-2-aminomethyl-9-deoxy-9-methylene-15-epi-16-methyl-16-phenyl-18,19,20-trinor-13,14-didehydro-PGF$_2$, a prostaglandin analog according to claim 111.

113. A prostaglandin analog according to claim 110, wherein at least one of R$_3$ and R$_4$ is fluoro.

114. 2-Decarboxy-2-aminomethyl-9-deoxy-9-methylene-15-epi-16,16-difluoro-16-phenyl-17,18,19,20-tetranor-13,14-didehydro-PGF$_2$, a prostaglandin according to claim 113.

115. A prostaglandin analog according to claim 110, wherein R$_3$ and R$_4$ are both hydrogen.

116. 2-Decarboxy-2-aminomethyl-9-deoxy-9-methylene-15-epi-15-methyl-16-phenyl-17,18,19,20-tetranor-13,14-didehydro-PGF$_2$, a prostaglandin analog according to claim 115.

117. A prostaglandin analog according to claim 104, wherein M$_1$ is

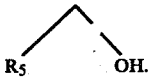

118. A porstaglandin analog according to claim 117, wherein s is zero or one and T is chloro, fluoro, or trifluoromethyl.

119. A prostaglandin analog according to claim 118, wherein g is 3.

120. A prostaglandin analog according to claim 119, wherein at least one of R$_3$ and R$_4$ is methyl.

121. 2-Decarboxy-2-aminomethyl-9-deoxy-9-methylene-2a,2b-dihomo-16-methyl-16-phenyl-18,19,20-trinor-13,14-didehydro-PGF$_2$, a prostaglandin analog according to claim 120.

122. A prostaglandin analog according to claim 119, wherein at least one of R$_3$ and R$_4$ is fluoro.

123. 2-Decarboxy-2-aminomethyl-9-deoxy-9-methylene-2a,2b-dihomo-16,16-difluoro-16-phenyl-17,18,19,20-tetranor-13,14-didehydro-PGF$_2$, a prostaglandin analog according to claim 122.

124. A prostaglandin analog according to claim 119, wherein R$_3$ and R$_4$ are both hydrogen.

125. 2-Decarboxy-2-aminomethyl-9-deoxy-9-methylene-2a,2b-dihomo-16-phenyl-17,18,19,20-tetranor-15-methyl-13,14-didehydro-PGF$_2$, a prostaglandin analog according to claim 124.

126. A prostaglandin analog according to claim 118 wherein g is one.

127. A prostaglandin analog according to claim 126, wherein at least one of R$_3$ and R$_4$ is methyl.

128. A prostaglandin analog according to claim 127, wherein R$_3$ and R$_4$ are both methyl.

129. 2-Decarboxy-2-aminomethyl-9-deoxy-9-methylene-16-methyl-16-phenyl-18,19,20-trinor-13,14-didehydro-PGF$_2$, a prostaglandin analog according to claim 128.

130. A prostaglandin analog according to claim 126, wherein at least one of R$_3$ and R$_4$ is fluoro.

131. A prostaglandin analog according to claim 130, wherein R$_3$ and R$_4$ are both fluoro.

132. A prostaglandin analog according to claim 131, wherein R$_5$ is methyl.

133. 2-Decarboxy-2-aminomethyl-9-deoxy-9-methylene-15-methyl-16,16-difluoro-16-phenyl-17,18,19,20-tetranor-13,14-didehydro-PGF$_2$, a prostaglandin analog according to claim 132.

134. A prostaglandin analog according to claim 131, wherein R$_5$ is hydrogen.

135. 2-Decarboxy-2-aminomethyl-9-deoxy-9-methylene-16,16-difluoro-16-phenyl-17,18,19,20-tetranor-13,14-didehydro-PGF$_2$, a prostaglandin analog according to claim 134.

136. A prostaglandin analog according to claim 126, wherein R$_3$ and R$_4$ are both hydrogen.

137. A prostaglandin analog according to claim 136, wherein R$_5$ is methyl.

138. 2-Decarboxy-2-aminomethyl-9-deoxy-9-methylene-15-methyl-16-phenyl-17,18,19,20-tetranor-13,14-didehydro-PGF$_2$, a prostaglandin analog according to claim 137.

139. A prostaglandin analog according to claim 136, wherein R$_5$ is hydrogen.

140. 2-Decarboxy-2-aminomethyl-9-deoxy-9-methylene-16-phenyl-17,18,19,20-tetranor-13,14-didehydro-PGF$_2$, a prostaglandin analog according to claim 139.

141. A prostaglandin analog according to claim 1, wherein Y$_1$ is trans—CH=CH—.

142. A prostaglandin analog according to claim 141, wherein

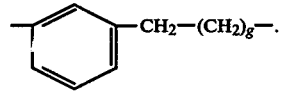

143. 2-Decarboxy-2-aminomethyl-9-deoxy-9-methylene-3,7-inter-m-phenylene-16-phenyl-4,5,6,17,18,19,20-heptanor-PGF$_1$, a prostaglandin analog according to claim 142.

144. A prostaglandin analog according to claim 141, wherein

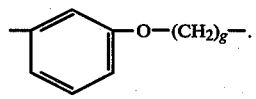

145. 2-Decarboxy-2-aminomethyl-9-deoxy-9-methylene-3,7-inter-m-phenylene-3-oxa-16-phenyl-4,5,6,17,18,19,20-heptanor-PGF$_1$, a prostaglandin analog according to claim 144.

146. A prostaglandin analog according to claim 141, wherein $Z_1$ is cis—CH$_2$—CH=CH—(CH$_2$)$_g$—CH$_2$—.

147. 2-Decarboxy-2-aminomethyl-9-deoxy-9-methylene-cis-4,5-didehydro-16-phenyl-17,18,19,20-tetranor-PGF$_1$, a prostaglandin analog according to claim 146.

148. A prostaglandin analog according to claim 141, wherein $Z_1$ is —CH$_2$—O—CH$_2$—(CH$_2$)$_h$—CH$_2$—.

149. 2-Decarboxy-2-aminomethyl-9-deoxy-9-methylene-5-oxa-16-phenyl-17,18,19,20-tetranor-PGF$_1$, a prostaglandin analog according to claim 148.

150. A prostaglandin analog according to claim 141, wherein $Z_1$ is —C≡C—CH$_2$—(CH$_2$)$_g$—CH$_2$—.

151. 2-Decarboxy-2-aminomethyl-9-deoxy-9-methylene-4,5-didehydro-16-phenyl-17,18,19,20-tetranor-PGF$_2$, a prostaglandin analog according to claim 150.

152. A prostaglandin analog according to claim 141, wherein $Z_1$ is —CH$_2$—C≡C—(CH$_2$)$_g$—CH$_2$—.

153. 2-Decarboxy-2-aminomethyl-9-deoxy-9-methylene-4,4,5,5-tetradehydro-16-phenyl-17,18,19,20-tetranor-PGF$_1$, a prostaglandin analog according to claim 152.

154. A prostaglandin analog according to claim 141, wherein $Z_1$ is —(CH$_2$)$_3$—(CH$_2$)$_g$—CH$_2$—.

155. A prostaglandin analog according to claim 154, wherein $M_1$ is

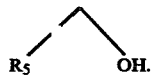

156. 2-Decarboxy-2-aminomethyl-9-deoxy-9-methylene-15-epi-16-phenyl-17,18,19,20-tetranor-PGF$_1$, a prostaglandin analog according to claim 155.

157. A prostaglandin analog according to claim 154, wherein $M_1$ is

158. A prostaglandin analog according to claim 157, wherein s is zero or one and T is chloro, fluoro, or trifluoromethyl.

159. A prostaglandin analog according to claim 158, wherein g is 3.

160. 2-Decarboxy-2-aminomethyl-9-deoxy-9-methylene-2a,2b-dihomo-15-methyl-16-phenyl-17,18,19,20-tetranor-PGF$_1$, a prostaglandin analog according to claim 159.

161. 2-Decarboxy-2-aminomethyl-9-deoxy-9-methylene-2a,2b-dihomo-16-phenyl-17,18,19,20-tetranor-PGF$_1$, a prostaglandin analog according to claim 159.

162. A prostaglandin analog according to claim 158, wherein g is one.

163. A prostaglandin analog according to claim 162, wherein at least one of $R_3$ and $R_4$ is methyl.

164. A prostaglandin analog according to claim 173, wherein $R_3$ and $R_4$ are both methyl.

165. 2-Decarboxy-2-aminomethyl-9-deoxy-9-methylene-16-methyl-16-phenyl-18,19,20-trinor-PGF$_1$, a prostaglandin analog according to claim 164.

166. A prostaglandin analog according to claim 162, wherein at least one of $R_3$ and $R_4$ is fluoro.

167. A prostaglandin analog according to claim 166, wherein $R_3$ and $R_4$ are both fluoro.

168. 2-Decarboxy-2-aminomethyl-9-deoxy-9-methylene-16,16-difluoro-16-phenyl-17,18,19,20-tetranor-PGF$_1$, a prostaglandin analog according to claim 167.

169. A prostaglandin analog according to claim 162, wherein $R_3$ and $R_4$ are both hydrogen.

170. A prostaglandin analog according to claim 169, wherein $R_5$ is methyl.

171. 2-Decarboxy-2-aminomethyl-9-deoxy-9-methylene-15-methyl-16-phenyl-17,18,19,20-tetranor-PGF$_1$, a prostaglandin analog according to claim 170.

172. A prostaglandin analog according to claim 169, wherein $R_5$ is hydrogen.

173. 2-Decarboxy-2-aminomethyl-9-deoxy-9-methylene-16-phenyl-17,18,19,20-tetranor-PGF$_1$, a prostaglandin analog according to claim 172.

174. A prostaglandin analog accordin to claim 141, wherein $Z_1$ is cis—CH=CH—CH$_2$—(CH$_2$)$_g$—CH$_2$—.

175. A prostaglandin analog according to claim 174, wherein $M_1$ is

176. A prostaglandin analog according to claim 175, wherein s is zero or one and T is chloro, fluoro, or trifluoromethyl.

177. A prostaglandin analog according to claim 176, wherein g is 3.

178. 2-Decarboxy-2-aminomethyl-9-deoxy-9-methylene-2a,2b-dihomo-15-epi-15-methyl-16-phenyl-17,18,19,20-tetranor-PGF$_2$, a prostaglandin analog according to claim 177.

179. 2-Decarboxy-2-aminomethyl-9-deoxy-9-methylene-2a,2b-dihomo-15-epi-16-phenyl-17,18,19,20-tetranor-PGF$_2$, a prostaglandin analog according to claim 177.

180. A prostaglandin analog according to claim 176, wherein g is one.

181. A prostaglandin analog according to claim 180, wherein at least one of $R_3$ and $R_4$ is methyl.

182. 2-Decarboxy-2-aminomethyl-9-deoxy-9-methylene-15-epi-16-methyl-16-phenyl-18,19,20-trinor-PGF$_2$, a prostaglandin analog according to claim 181.

183. A prostaglandin analog according to claim 180, wherein at least one of $R_3$ and $R_4$ is fluoro.

184. 2-Decarboxy-2-aminomethyl-9-deoxy-9-methylene-15-epi-16,16-difluoro-16-phenyl-17,18,19,20-tetranor-PGF$_2$, a prostaglandin analog according to claim 183.

185. A prostaglandin analog according to claim 180, wherein $R_3$ and $R_4$ are both hydrogen.

186. 2-Decarboxy-2-aminomethyl-9-deoxy-9-methylene-15-epi-15-methyl-16-phenyl-17,18,19,20-tetranor-PGF$_2$, a prostaglandin analog according to claim 185.

187. A prostaglandin analog according to claim 174, wherein $M_1$ is

188. A prostaglandin analog according to claim 187, wherein s is zero or one and T is chloro, fluoro, or trifluoromethyl.

189. A prostaglandin analog according to claim 188, wherein g is 3.

190. A prostaglandin analog according to claim 189, wherein at least one of $R_3$ and $R_4$ is methyl.

191. 2-Decarboxy-2-aminomethyl-9-deoxy-9-methylene-2a,2b-dihomo-16-methyl-16-phenyl-18,19,20-trinor-PGF$_2$, a prostaglandin analog according to claim 190.

192. A prostaglandin analog according to claim 189, wherein at least one of $R_3$ and $R_4$ is fluoro.

193. 2-Decarboxy-2-aminomethyl-9-deoxy-9-methylene-2a,2b-dihomo-16,16-difluoro-16-phenyl-17,18,19,20-tetranor-PGF$_2$, a prostaglandin analog according to claim 190.

194. A prostaglandin analog according to claim 189, wherein $R_3$ and $R_4$ are both hydrogen.

195. 2-Decarboxy-2-aminomethyl-9-deoxy-9-methylene-2a,2b-dihomo-15-methyl-16-phenyl-17,18,19,20-tetranor-PGF$_2$, a prostaglandin analog according to claim 194.

196. A prostaglandin analog according to claim 188, wherein g is one.

197. A prostaglandin analog according to claim 196, wherein at least one of $R_3$ and $R_4$ is methyl.

198. A prostaglandin analog according to claim 197, wherein $R_3$ and $R_4$ are both methyl.

199. 2-Decarboxy-2-aminomethyl-9-deoxy-9-methylene-16-methyl-16-phenyl-18,19,20-trinor-PGF$_2$, a prostaglandin analog according to claim 198.

200. A prostaglandin analog according to claim 196, wherein at least one of $R_3$ and $R_4$ is fluoro.

201. A prostaglandin analog according to claim 200, wherein $R_3$ and $R_4$ are both fluoro.

202. A prostaglandin analog according to claim 201, wherein $R_5$ is methyl.

203. 2-Decarboxy-2-aminomethyl-9-deoxy-9-methylene-15-methyl-16,16-difluoro-16-phenyl-17,18,19,20-tetranor-PGF$_2$, a prostaglandin analog according to claim 202.

204. A prostaglandin analog according to claim 201, wherein $R_5$ is hydrogen.

205. 2-Decarboxy-2-aminomethyl-9-deoxy-9-methylene-16,16-difluoro-16-phenyl-17,18,19,20-tetranor-PGF$_2$, a prostaglandin analog according to claim 204.

206. A prostaglandin analog according to claim 204, wherein $R_3$ and $R_4$ are both hydrogen.

207. A prostaglandin analog according to claim 206, wherein $R_5$ is methyl.

208. 2-Decarboxy-2-aminomethyl-9-deoxy-9-methylene-15-methyl-16-phenyl-17,18,19,20-tetranor-PGF$_2$, a prostaglandin analog according to claim 207.

209. A prostaglandin analog according to claim 206, wherein $R_5$ is hydrogen.

210. 2-Decarboxy-2-aminomethyl-9-deoxy-9-methylene-16-phenyl-17,18,19,20-tetranor-PGF$_2$, a prostaglandin analog according to claim 209.

* * * * *

UNITED STATES PATENT OFFICE
CERTIFICATE OF CORRECTION

Patent No. 4,191,707          Dated  4 March 1980

Inventor(s)  G. L. Bundy

It is certified that error appears in the above-identified patent and that said Letters Patent are hereby corrected as shown below:

Column 1, lines 18-26,

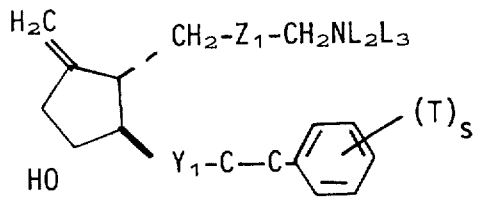

should read

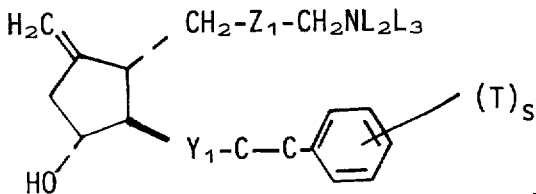

Signed and Sealed this

Twenty-third Day of September 1980

[SEAL]

Attest:

SIDNEY A. DIAMOND

Attesting Officer    Commissioner of Patents and Trademarks